US006842021B1

(12) United States Patent
Weaver et al.

(10) Patent No.: US 6,842,021 B1
(45) Date of Patent: Jan. 11, 2005

(54) SYSTEM AND METHOD FOR DETECTING LOCATION OF A DEFECTIVE ELECTRICAL CONNECTION WITHIN AN INTEGRATED CIRCUIT

(75) Inventors: Kevin Weaver, San Jose, CA (US); Gengying Gao, Fremont, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 0 days.

(21) Appl. No.: 10/704,404

(22) Filed: Nov. 7, 2003

(51) Int. Cl.[7] .............................................. G01R 31/302
(52) U.S. Cl. ...................................... 324/752; 324/750
(58) Field of Search ........................ 324/750, 752–754, 324/758; 438/4–18, 115; 250/307

(56) References Cited

U.S. PATENT DOCUMENTS

| | | | | |
|---|---|---|---|---|
| 4,242,635 A | * | 12/1980 | Burns | 324/753 |
| 4,466,746 A | * | 8/1984 | Hancock et al. | 324/158.1 |
| 4,668,916 A | * | 5/1987 | Pech | 324/456 |
| 4,682,857 A | | 7/1987 | Tan | |
| 6,121,059 A | * | 9/2000 | Liu | 438/14 |
| 6,559,670 B1 | * | 5/2003 | Motamedi | 324/765 |
| 6,657,447 B1 | * | 12/2003 | Parandoosh | 324/760 |

OTHER PUBLICATIONS

Edward Cole Jr. et al.. Resistive Interconnection Localization, 27th Annual International Symposium for Testing and Failure Analysis, Nov. 11–15, 2001, Santa Clara, California.

* cited by examiner

Primary Examiner—Michael Tokar
Assistant Examiner—Jermele Hollington
(74) Attorney, Agent, or Firm—Vedder Price Kaufman & Kammholz, P.C.

(57) ABSTRACT

A method and system for detecting the location of a defect within an integrated circuit (IC). With power applied to the IC via its power supply terminals (VDD, VSS), an infrared (IR) laser light is scanned along the X and Y dimensions of a surface of the IC. Reflected IR light and the IC power supply current are measured and processed using Fourier Transformation computations. Based upon the results of such computations, the Z coordinate is determined that corresponds to the depth of the defect within the IC.

14 Claims, 3 Drawing Sheets

SYSTEM AND METHOD FOR DETECTING LOCATION OF A DEFECTIVE ELECTRICAL CONNECTION WITHIN AN INTEGRATED CIRCUIT

BACKGROUND OF THE INVENTION

1. Field of the Invention

The present invention relates to failure analysis techniques for integrated circuits (ICs), and in particular, to systems and methods for detecting locations of defective electrical connections within ICs.

2. Description of the Related Art

As ICs have become increasingly complex and capable of more functions, in terms of both quantities and varieties, the electrical interconnections between the various devices and functional blocks increasingly have become of more significant concern. Such electrical interconnections, which are necessarily resistive (albeit ideally with small resistances), include interconnections between the various layers of semiconductor material(s) and metal within an IC. These interlayer connections include contacts and vias which are necessarily fabricated in parts as the successive layers of the IC are deposited or otherwise developed.

There are many failure mechanisms for these vias, so with increasing numbers of vias in an IC it is increasingly important that failures be diagnosed, located and resolved as quickly as possible. Many conventional techniques have been used to test for hot spots on the surface of an IC, including infrared optical microscopy, light emission microscopy, transistor logic state mapping, induced thermal effect imaging and scanning laser microscopy. (A discussion of scanning laser microscopy can be found in Cole Jr. et al., "Resistive Interconnection Localization", Proceeding from the 27th International Symposium for Testing and Failure Analysis, November 11–15, 2001, Santa Clara, Calif., the contents of which are incorporated herein by reference.)

Once these hot spots are found, the x and y coordinates are noted and de-processing of the IC is begun. Since there are multiple successive layers on the IC, the de-processing must be performed layer by layer from the top to the bottom in order to determine where the hot spots originate. Generally, a Reaction of Ion Etching (RIE) system is used to remove each layer of the IC, following which the IC is then placed under a Scanning Electron Microscope (SEM) for the failure analysis (FA) engineers to find the defect. If no defect is found, the next layer is removed. Both RIE and SEM must be operated in vacuum environments, thereby requiring a significant amount of time due to the venting and pumping required. As a result, much time is consumed in locating the defect, especially with an IC containing many layers. Further, the actual defect can sometimes be missed or damaged such that its failure mechanism cannot be determined.

SUMMARY OF THE INVENTION

In accordance with the presently claimed invention, a method and system are provided for detecting the location of a defect within an integrated circuit (IC). With power applied to the IC via its power supply terminals (VDD, VSS), an infrared (IR) laser light is scanned along the X and Y dimensions of a surface of the IC. Reflected IR light and the IC power supply current are measured and processed using Fourier Transformation computations. Based upon the results of such computations, the Z coordinate is determined that corresponds to the depth of the defect within the IC.

In accordance with one embodiment of the presently claimed invention, a method of detecting the location of a defect within an integrated circuit (IC) includes:

providing an IC with a plurality of layers including one or more metal layers and a generally planar surface having X and Y dimensions;

applying power to the IC at a substantially constant source voltage with a measurable source current;

exposing the IC to a laser light, including scanning with the laser light along at least a portion of the X and Y dimensions, with a plurality of controllable focal lengths corresponding to at least the plurality of metal layers;

converting infrared (IR) light reflected from the IC during at least a portion of the exposing of the IC to an IR signal;

processing the IR signal in accordance with a first Fourier Transformation computation;

determining a first one of the plurality of controllable focal lengths corresponding to a selected value of the processed IR signal;

measuring the source current during the exposing of the IC;

processing the measured source current in accordance with a second Fourier Transformation computation;

determining a second one of the plurality of controllable focal lengths corresponding to the selected value of the processed source current; and determining a Z coordinate generally orthogonal to the IC surface and corresponding to a difference between the first and second focal lengths.

In accordance with another embodiment of the presently claimed invention, a system for detecting the location of a defect within an integrated circuit (IC) includes power source circuitry, a scanning laser source, conversion circuitry, measurement circuitry and processing circuitry. The power source circuitry is to supply power to an IC at a substantially constant source voltage with a measurable source current, wherein the IC comprises a plurality of layers including one or more metal layers and a generally planar surface having X and Y dimensions. The scanning laser source is to expose the IC to a laser light, including to scan with the laser light along at least a portion of the X and Y dimensions, with a plurality of controllable focal lengths corresponding to at least the plurality of metal layers. The conversion circuitry is responsive to infrared (IR) light reflected from the IC during at least a portion of the exposing of the IC by providing an IR signal. The measurement circuitry is responsive to the source current during the exposing of the IC by providing a current measurement signal. The processing circuitry is responsive to the IR and current measurement signals by: processing the IR signal in accordance with a first Fourier Transformation computation; determining a first one of the plurality of controllable focal lengths corresponding to a selected value of the processed IR signal; processing the current measurement signal in accordance with a second Fourier Transformation computation; determining a second one of the plurality of controllable focal lengths corresponding to the selected value of the processed current measurement signal; and determining a Z coordinate generally orthogonal to the IC surface and corresponding to a difference between the first and second focal lengths.

In accordance with still another embodiment of the presently claimed invention, a system for detecting the location of a defect within an integrated circuit (IC) includes power means, laser means, converter means, measuring means and processor means. The power means is for applying power to an IC at a substantially constant source voltage with a measurable source current, wherein the IC comprises a plurality of layers including one or more metal layers and a generally planar surface having X and Y dimensions. The laser means is for exposing the IC to a laser light, including scanning with the laser light along at least a portion of the X and Y dimensions, with a plurality of controllable focal lengths corresponding to at least the plurality of metal layers. The converter means is for converting infrared (IR) light reflected from the IC during at least a portion of the exposing of the IC to an IR signal. The measuring means is for measuring the source current during the exposing of the IC. The processor means is for: processing the IR signal in accordance with a first Fourier Transformation computation; determining a first one of the plurality of controllable focal lengths corresponding to a selected value of the processed IR signal; processing the measured source current in accordance with a second Fourier Transformation computation; determining a second one of the plurality of controllable focal lengths corresponding to the selected value of the processed source current; and determining a Z coordinate generally orthogonal to the IC surface and corresponding to a difference between the first and second focal lengths.

DETAILED DESCRIPTION OF THE INVENTION

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Throughout the present disclosure, absent a clear indication to the contrary from the context, it will be understood that individual circuit elements as described may be singular or plural in number. For example, the terms "circuit" and "circuitry" may include either a single component or a plurality of components, which are either active and/or passive and are connected or otherwise coupled together (e.g., as one or more integrated circuit chips) to provide the described function. Additionally, the term "signal" may refer to one or more currents, one or more voltages, one or more optical signals, or a data signal. Within the drawings, like or related elements will have like or related alpha, numeric or alphanumeric designators.

Figure 1:
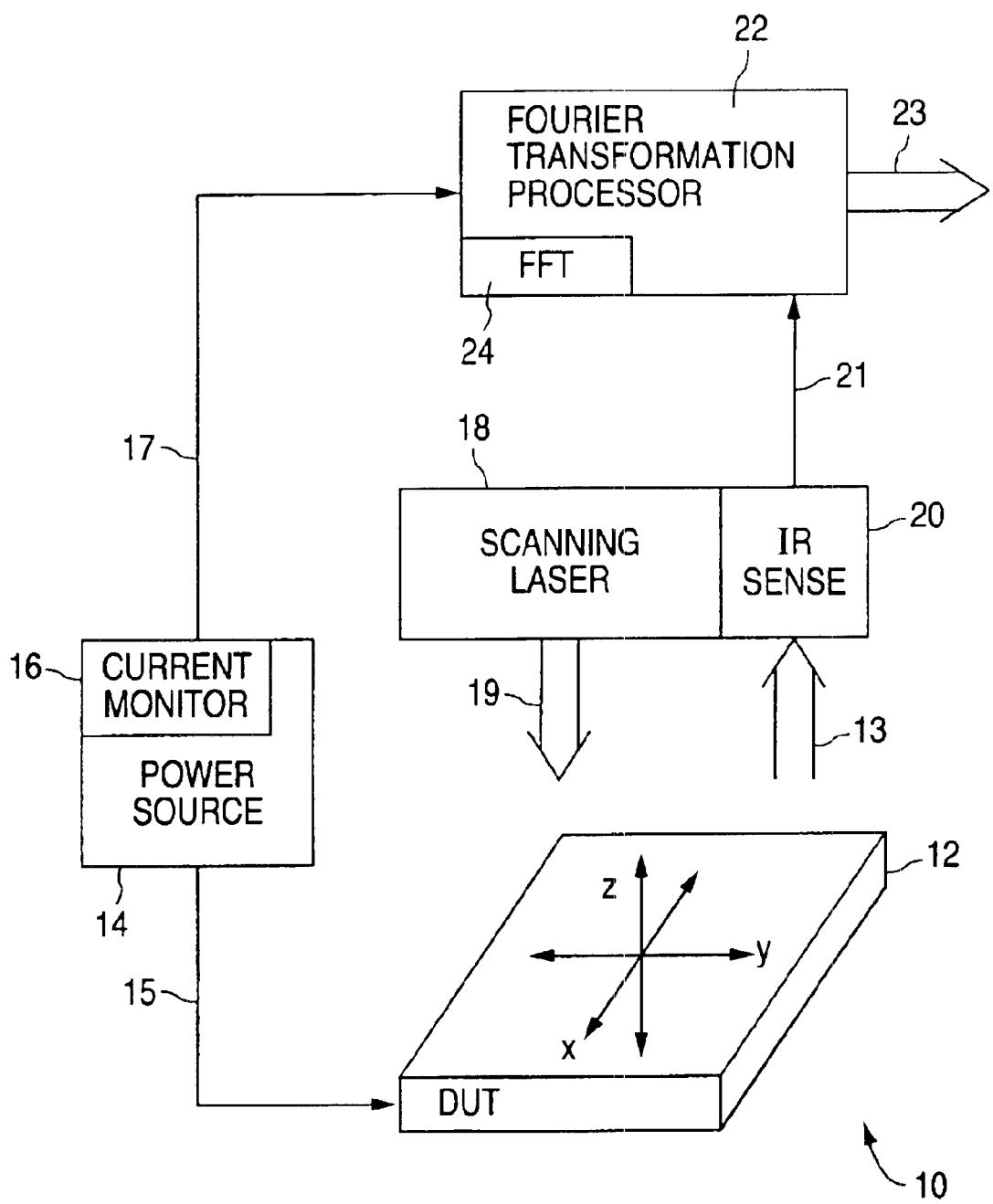
FIG. 1 depicts a system for detecting a location of a defect within an IC in accordance with one embodiment of the presently claimed invention.

Referring to FIG. 1, a system 10 for detecting the location of a defect within an IC under test 12 in accordance with one embodiment of the presently claimed invention includes a power source 14 with some form of output current monitor 16, a scanning laser 18, an infrared (IR) sensing device 20, and a Fourier Transform Processor 22 with the capability 24 of performing Fourier Transformation processes (e.g., fast Fourier Transformations (FFT)) of the IR 21 and current test 17 signals. Operation of this system 10 is generally as follows.

The device under test (DUT) 12 is an IC which is generally planar in form and having a finite thickness, thereby having length, width and depth (or thickness) dimensions with corresponding x, y and z coordinates, respectively. The IC 12 receives power 15 (at a fixed power supply voltage with a variable power supply current) from the power source 14 which uses a current monitor 16 to monitor the amount of current drawn by the IC 12 during testing. A current test signal 17 (which may be electrical or optical) is provided indicating, in real time, the amount of current drawn by the IC 12 during testing.

The scanning laser system 18, e.g., a scanning laser microscope, emits a laser beam 19 with a wavelength of approximately 1340 nanometers (the wavelength at which silicon is relatively transparent) and scans the IC 12 along its x and y dimensions, e.g., in a raster fashion, with a focal length corresponding to the z dimension of the IC layer being scanned (discussed in more detail below). During this scanning of the laser 19, the IC 12 reflects IR light 13 which is detected by the IR sensor 20 and converted to an IR test signal 21 (which may be electrical or optical).

The current 17 and IR 21 test signals are processed by the processor 22 by transforming such signals 17, 21 in accordance with Fourier Transformation computations. In accordance with a preferred embodiment, one or more FFT algorithms 24 are used to process these signals 17, 21 to generate a set 23 of signals representing the intensities, or magnitudes, of these signals 17, 21 in the frequency domain.

Figure 2:
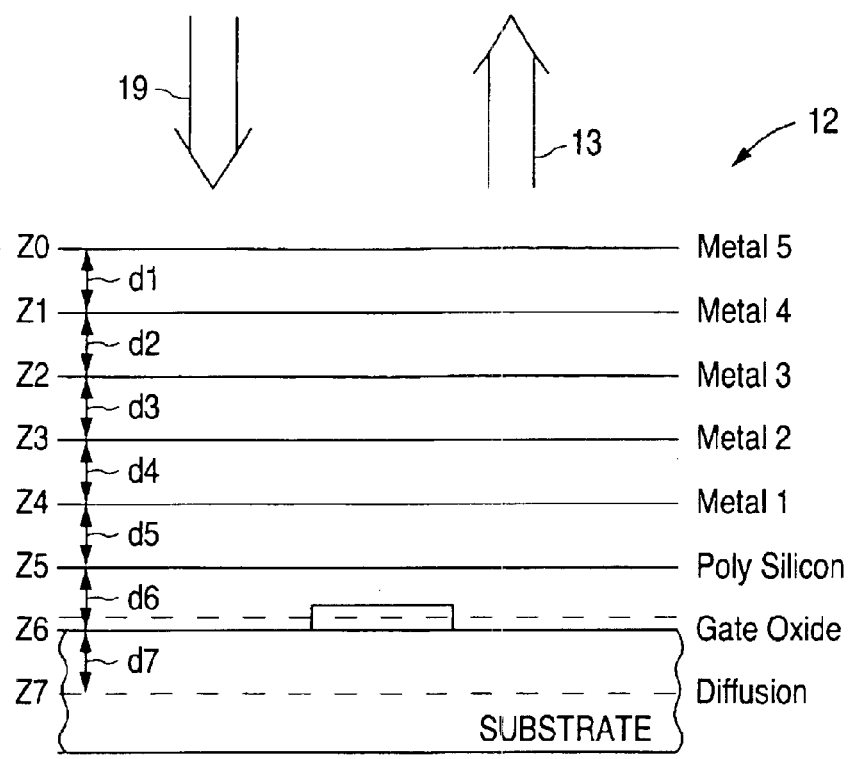
FIG. 2 depicts a representation of a cross-section of an IC having multiple layers of metal being tested in accordance with the presently claimed invention.

Referring to FIG. 2, the scanning of the IC 12 with the laser beam 19 at different focal lengths can be better understood. In this example, the IC, represented here in cross-section, includes a substrate containing a diffusion layer and having a surface upon which gate oxide is applied, followed by successive layers including polysilicon and a number (e.g., five) of metal layers. For the top, or last, metal layer, the focal length of the laser beam 19 has a z coordinate Z0. Once this layer has been scanned, the next layer of metal is scanned with a focal length of Z1, which equals the focal length Z0 plus the distance d1 between metal layers 5 and 4. Similarly, the next metal layer is scanned with a focal length of Z2 which is equal to the focal length Z1 of metal layer 4 plus the distance d2 between metal layers 4 and 3, or alternatively, the focal length Z0 of metal layer 5 plus the distance d1+d2 between metal layers 5 and 3. This scanning process is repeated for the remaining metal layers, as well as the polysilicon layer (focal length Z5), gate oxide layer (focal length Z6) and diffusion layer (focal length Z7), as desired.

Once this scanning of the IC 12 has been completed, the processed signals 23 will indicate the location of any defect within the IC 12 by determining the x, y and z coordinates corresponding to the processed signals 23 having the maximum magnitudes corresponding to the highest intensities.

Figure 3:
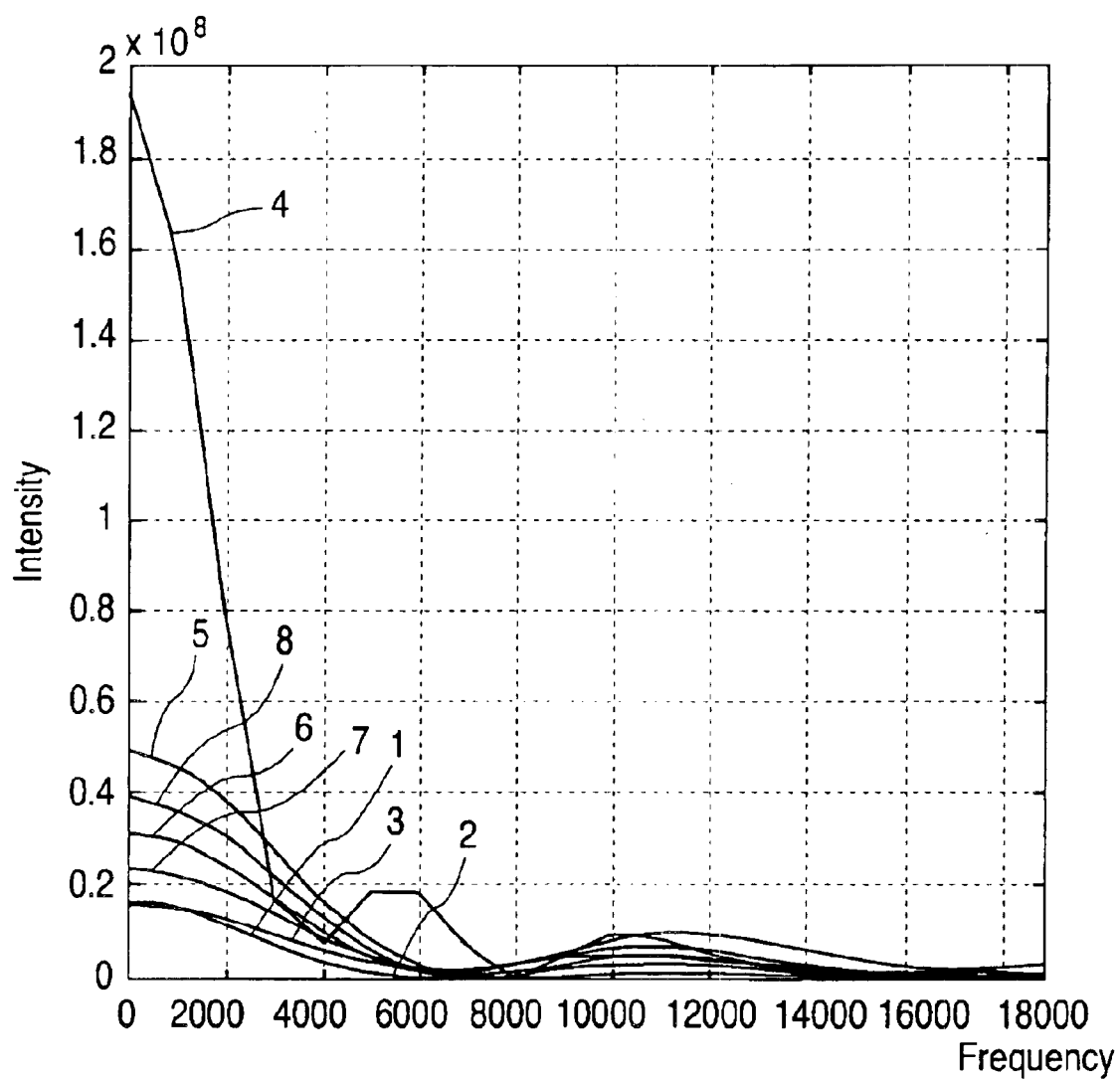
FIG. 3 is a graph of intensity versus frequency for a transformed signal corresponding to the infrared light reflected from the IC under test during testing in accordance with the presently claimed invention.

Referring to FIG. 3, as discussed above, the reflected IR light 13 is converted to an IR test signal 21 which is processed in accordance with Fourier Transformation computations to produce a subset of the set 23 of processed signals. In this graph, the eight signals corresponding to the eight scanned layers of the IC (FIG. 2) are plotted according to their intensity over frequency. The curve numbered 4, which has the highest intensity, corresponds to the reflected IR light from the top metal layer. For example, in one test using the presently claimed invention, this corresponded to a scanning laser beam 19 having a focal length of 64,870 micrometers. The remaining curves, numbered 1–3 and 5–8 are for the remaining layers of the IC 12.

Figure 4:
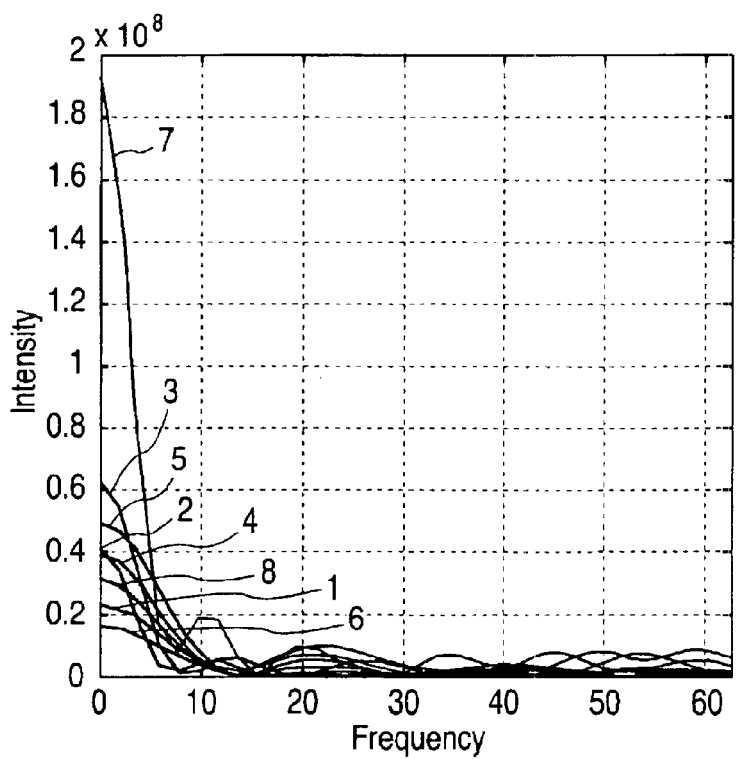
FIG. 4 is a graph of intensity versus frequency for a transformed signal corresponding to the thermal induced voltage alternative (TIVA) signal for the IC under test during testing in accordance with the presently claimed invention.

Referring to FIG. 4, as discussed above, the current test signal 17 representing the current drawn by the IC 12 during testing in real time, is processed by the processor 22 to produce another subset of the set 23 of processed signals. The curve numbered 7 in the graph corresponds to the metal layer (FIG. 2) having a scanning laser beam 19 focal length of 64,874 micrometers. The remaining curves, numbered 1–6 and 8, correspond to the remaining layers within the IC 12.

Combining these two results provide the z coordinate, or depth, of the defect. Hence, for this example, the depth of the defect is at 64, 874−64, 870=4 micrometers. Using this number, de-processing of the IC 12 is done down to the IC layer at this depth, following which the failure analysis can proceed with the knowledge that the analysis is being performed at the proper depth, i.e., on the appropriate layer, within the IC 12.

Determining the x and y coordinates of a defect can be done in accordance with any of a number of conventional failure analysis techniques, including the use of liquid crystal materials with temperature control to detect hot spots on the surface of the IC 12. (One example of such a technique is described in U.S. Pat. No. 4,682,857, the disclosure of which is incorporated herein by reference.)

Various other modifications and alternations in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of detecting the location of a defect within an integrated circuit (IC), comprising:

providing an IC with a plurality of layers including one or more metal layers and a generally planar surface having X and Y dimensions;

applying power to said IC at a substantially constant source voltage with a measurable source current;

exposing said IC to a laser light, including scanning with said laser light along at least a portion of said X and Y dimensions, with a plurality of controllable focal lengths corresponding to at least said plurality of metal layers;

converting infrared (IR) light reflected from said IC during at least a portion of said exposing of said IC to an IR signal;

processing said IR signal in accordance with a first Fourier Transformation computation;

determining a first one of said plurality of controllable focal lengths corresponding to a selected value of said processed IR signal;

measuring said source current during said exposing of said IC;

processing said measured source current in accordance with a second Fourier Transformation computation;

determining a second one of said plurality of controllable focal lengths corresponding to said selected value of said processed source current; and determining a Z coordinate generally orthogonal to said IC surface and corresponding to a difference between said first and second focal lengths.

2. The method of claim 1, wherein said determining a first one of said plurality of controllable focal lengths corresponding to a selected value of said processed IR signal comprising determining a first one of said plurality of controllable focal lengths corresponding to a top one of said one or more metal layers.

3. The method of claim 2, wherein said determining a first one of said plurality of controllable focal lengths corresponding to a selected value of said processed IR signal comprises determining a first one of said plurality of controllable focal lengths corresponding to a maximum value of said processed IR signal.

4. The method of claim 1, wherein said determining a first one of said plurality of controllable focal lengths corresponding to a selected value of said processed IR signal comprises determining a first one of said plurality of controllable focal lengths corresponding to a maximum value of said processed IR signal.

5. The method of claim 1, wherein:

said processing said IR signal in accordance with a first Fourier Transformation computation comprises processing said IR signal in accordance with a selected Fast Fourier Transform (FFT) algorithm; and said processing said measured source current in accordance with a second Fourier Transformation computation comprises processing said measured source current in accordance with said selected FFT algorithm.

6. The method of claim 1, wherein:

said processing said IR signal in accordance with a first Fourier Transformation computation comprises processing said IR signal in accordance with a first Fast Fourier Transform (FFT) algorithm; and said processing said measured source current in accordance with a second Fourier Transformation computation comprises processing said measured source current in accordance with a second FFT algorithm.

7. An apparatus including a system for detecting the location of a defect within an integrated circuit (IC), comprising:

power source circuitry to supply power to an IC at a substantially constant source voltage with a measurable source current, wherein said IC comprises a plurality of layers including one or more metal layers and a generally planar surface having X and Y dimensions;

a scanning laser source to expose said IC to a laser light, including to scan with said laser light along at least a portion of said X and Y dimensions, with a plurality of controllable focal lengths corresponding to at least said plurality of metal layers;

conversion circuitry responsive to infrared (IR) light reflected from said IC during at least a portion of said exposing of said IC by providing an IR signal;

measurement circuitry responsive to said source current during said exposing of said IC by providing a current measurement signal; and processing circuitry responsive to said IR and current measurement signals by processing said IR signal in accordance with a first Fourier Transformation computation, determining a first one of said plurality of controllable focal lengths corresponding to a selected value of said processed IR signal, processing said current measurement signal in accordance with a second Fourier Transformation computation, determining a second one of said plurality of controllable focal lengths corresponding to said selected value of said processed current measurement signal, and determining a Z coordinate generally orthogonal to said IC surface and corresponding to a difference between said first and second focal lengths.

8. The apparatus of claim 7, wherein said scanning laser source comprises a scanning laser microscope.

9. The apparatus of claim 7, wherein said responsiveness by said processing circuitry to said IR and current measurement signals comprises determining a first one of said plurality of controllable focal lengths corresponding to a top one of said one or more metal layers.

10. The apparatus of claim 9, wherein said responsiveness by said processing circuitry to said IR and current measurement signals comprises determining a first one of said plurality of controllable focal lengths corresponding to a maximum value of said processed IR signal.

11. The apparatus of claim 7, wherein said responsiveness by said processing circuitry to said IR and current measurement signals comprises determining a first one of said plurality of controllable focal lengths corresponding to a maximum value of said processed IR signal.

12. The apparatus of claim 7, wherein said responsiveness by said processing circuitry to said IR and current measurement signals comprises:

processing said IR signal in accordance with a selected Fast Fourier Transform (FFT) algorithm; and processing said current measurement signal in accordance with said selected FFT algorithm.

13. The apparatus of claim 7, wherein said responsiveness by said processing circuitry to said IR and current measurement signals comprises:

processing said IR signal in accordance with a first Fast Fourier Transform (FFT) algorithm; and processing said current measurement signal in accordance with a second FFT algorithm.

14. An apparatus including a system for detecting the location of a defect within an integrated circuit (IC), comprising:

power means for applying power to an IC at a substantially constant source voltage with a measurable source current, wherein said IC comprises a plurality of layers including one or more metal layers and a generally planar surface having X and Y dimensions;

laser means for exposing said IC to a laser light, including scanning with said laser light along at least a portion of said X and Y dimensions, with a plurality of controllable focal lengths corresponding to at least said plurality of metal layers;

converter means for converting infrared (IR) light reflected from said IC during at least a portion of said exposing of said IC to an IR signal;

measuring means for measuring said source current during said exposing of said IC; and processor means for processing said IR signal in accordance with a first Fourier Transformation computation, determining a first one of said plurality of controllable focal lengths corresponding to a selected value of said processed IR signal, processing said measured source current in accordance with a second Fourier Transformation computation, determining a second one of said plurality of controllable focal lengths corresponding to said selected value of said processed source current, and determining a Z coordinate generally orthogonal to said IC surface and corresponding to a difference between said first and second focal lengths.

* * * * *

UNITED STATES PATENT AND TRADEMARK OFFICE
CERTIFICATE OF CORRECTION

PATENT NO. : 6,842,021 B1
DATED : January 11, 2005
INVENTOR(S) : Kevin Weaver and Gengying Gao It is certified that error appears in the above-identified patent and that said Letters Patent is hereby corrected as shown below:

Column 1,
Line 62, delete "(1R)" and insert -- (IR) --.

Column 2,
Lines 15 and 48, delete "(1R)" and insert -- (IR) --.

Column 3,
Line 12, delete "(1R)" and insert -- (IR) --.

Column 4,
Line 7, delete "(1R)" and insert -- (IR) --.

Column 5,
Line 10, delete "58" and insert -- 5-8 --.

Column 6,
Line 14, delete "comprising" and insert -- comprises --.

Signed and Sealed this

Twelfth Day of April, 2005

JON W. DUDAS
*Director of the United States Patent and Trademark Office*